United States Patent [19]

Ishibashi et al.

[11] Patent Number: 5,254,545
[45] Date of Patent: Oct. 19, 1993

[54] INJECTABLE PREPARATIONS CONTAINING CEPHALOSPORIN MEDICAMENT

[75] Inventors: Yasuo Ishibashi, Gifu; Isamu Hasegawa, Aichi; Masanori Kayano, Saitama; Ryoichi Machida, Chiba; Masahiro Kawahara, Ibaraki; Sumio Watanabe, Aichi, all of Japan

[73] Assignee: Eisai Co., Ltd., Tokyo, Japan

[21] Appl. No.: 589,922

[22] Filed: Sep. 28, 1990

[30] Foreign Application Priority Data

Sep. 30, 1989 [JP] Japan .................. 1-253782

[51] Int. Cl.$^5$ ........................... A61K 31/545
[52] U.S. Cl. ...................... 514/202; 540/222
[58] Field of Search ............... 540/222, 227; 514/202, 514/206

[56] References Cited

U.S. PATENT DOCUMENTS 4,822,785  4/1989  Ishibashi et al. ............ 540/222
4,921,850  5/1990  Kamiya et al. ............... 514/202

Primary Examiner—Nicholas S. Rizzo
Attorney, Agent, or Firm—Wenderoth, Lind & Ponack

[57] ABSTRACT

A preparation containing a cephalosporin medicament is disclosed. The preparation comprises a cephalosporin derivative represented by the following formula:

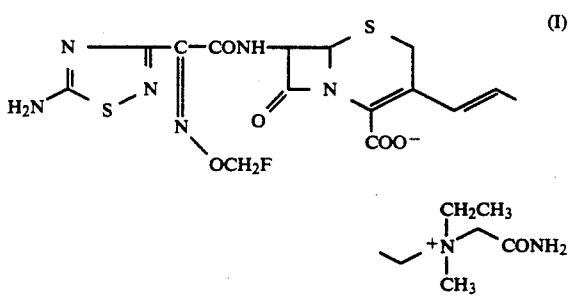

namely, 7β-{2-(5-amino-1,2,4-thiadiazol-3-yl)-(Z)-2-fluoromethoxyiminoacetamido}-3-{(E)-3-(carbamoyl-methylethylmethylammonio) -1-propen-1-yl}-3-cephem-4-carboxylate or a pharmaceutically acceptable salt thereof salt, lactose, citric acid or a sodium salt thereof, and arginine or a hydrochloride thereof; or the cephalosporin derivative represented by the formula (I) or a pharmaceutically acceptable salt thereof, lactose, citric acid or a sodium salt thereof, and sodium chloride.

1 Claim, No Drawings

INJECTABLE PREPARATIONS CONTAINING CEPHALOSPORIN MEDICAMENT

BACKGROUND OF THE INVENTION

1. Field of the Invention

The present invention relates to injectable preparations containing a cephalosporin medicament, which can be used effectively in the field of medicines.

2. Description of the Related Art

A cephalosporin represented by the following formula:

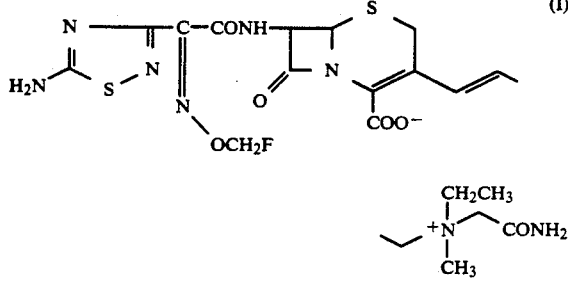

namely, 7β-{2-(5-amino-1,2,4-thiadiazol-3-yl)-(Z)-2-fluoromethoxyiminoacetamido}-3-{( E)-3-(carbamoylmethylethylmethylammonio)-1-propen-1-yl}-3-cephem-4-carboxylate and pharmaceutically acceptable salts thereof (hereinafter called "the above substances" for the sake of brevity) have a broad antibacterial spectrum ranging over Gram positive bacteria, Gram negative bacteria and anaerobic bacteria. In particular, they are highly useful cephem-series antibiotics capable of exhibiting strong antibacterial activities against resistant *Staphylococcus* and *Pseudomonas aeruginosa* and are expected to have utility as injections (Japanese Patent Application Laid-Open No. 156984/1989).

The above substances are however accompanied by the drawback that they are unstable and are susceptible to decomposition under high-temperature and/or high-humidity conditions, leading to content reduction and coloration.

Conventional stabilization methods for cephalosporin derivatives include the method disclosed in Japanese Patent Application Laid-Open No. 216996/1989 and the pharmaceutical preparations disclosed in Japanese Patent Application Laid-Open No. 37728/1986. According to the method, lactose, glucose, sucrose or galactose is added along with glycine to a cephalosporin derivative, followed by lyophilization. Each of the pharmaceutical preparations comprises ceftazidime, sodium carbonate and amorphous lactose. Neither the method nor the pharmaceutical preparations are however satisfactory to stabilize the above substances.

SUMMARY OF THE INVENTION

The present inventors have carried out an extensive investigation with a view toward formulating the above substances into stable injection. As a result, it has been found that the above substances can be stabilized and formulated into injectable preparations free from content reduction and coloration even under high-temperature and/or high-humidity conditions by formulating them together with lactose, citric acid or a sodium salt thereof and arginine or a hydrochloride thereof, or along with lactose, citric acid or a sodium salt thereof and sodium chloride into injectable preparations.

An object of the present invention is therefore to provide a stable injection containing the cephalosporin derivative of the formula (I) or a pharmaceutically acceptable salt thereof.

In one aspect of the present invention, there is thus provided a preparation containing a cephalosporin medicament. The preparation comprises a cephalosporin derivative represented by the following formula:

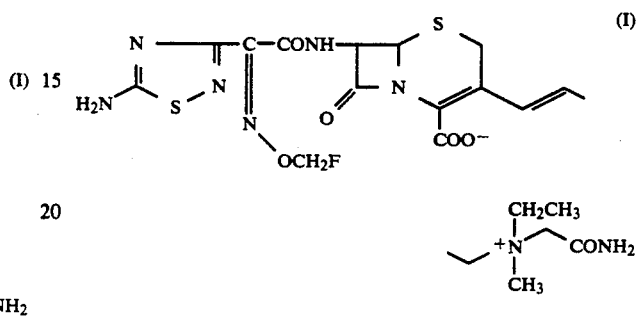

namely, 7β-{2-(5-amino-1,2,4-thiadiazol-3-yl)-(Z)-2-fluoromethoxyiminoacetamido}-3-{( E)-3-(carbamoylmethylethylmethylammonio)-1-propen-1-yl}-3-cephem-4-carboxylate or a pharmaceutically acceptable salt thereof salt, lactose, citric acid or a sodium salt thereof, and arginine or a hydrochloride thereof; or the cephalosporin derivative represented by the formula (I) or a pharmaceutically acceptable salt thereof, lactose, citric acid or a sodium salt thereof, and sodium chloride.

The content of the cephalosporin derivative of the formula (I) or the pharmaceutically acceptable salt thereof does not drop to any substantial extent during storage. Further, the preparation practically remains free from coloration and also has excellent resistance to variations in external appearance.

DETAILED DESCRIPTION OF THE INVENTION AND PREFERRED EMBODIMENTS

Illustrative of the pharmaceutically acceptable salt of the cephalosporin derivative represented by the formula (I) include acid addition salts such as hydrochloride, sulfate, citrate and tartrate in this invention.

Regarding the proportions of the individual ingredients in the preparation of the present invention, the preparation may generally contain 0.1–1.3 parts by weight of lactose, 0.01–0.065 part by weight of citric acid or a sodium salt thereof, and 0.1–0.65 part by weight of arginine or a hydrochloride thereof or sodium chloride, all per part by weight of the cephalosporin derivative represented by the formula (I) or the pharmaceutically acceptable salt thereof. Preferably, the preparation contains 0.2–1.0 part by weight of lactose, 0.02–0.05 part by weight of citric acid or a sodium salt thereof and 0.2–0.5 part by weight of arginine or a hydrochloride thereof or sodium chloride, all per part by weight of the cephalosporin derivative represented by the formula (I) or the pharmaceutically acceptable salt thereof. More preferably, the preparation contains 0.3–0.7 part by weight of lactose, 0.02–0.035 part by weight of citric acid or a sodium salt thereof and 0.2–0.35 part by weight of arginine or a hydrochloride thereof or sodium chloride, all per part by weight of the cephalosporin derivative represented by the formula (I) or the pharmaceutically acceptable salt thereof.

In the present invention, the preparation is formulated by adding citric acid or a sodium salt thereof or by incorporating citric acid or a sodium salt thereof and arginine or a hydrochloride thereof. In liquid and lyophilized preparations, these additives are considered to take various forms depending on the pH and the coexisting substances. Therefore, the terms "citric acid or a sodium salt thereof" and "arginine or a hydrochloride thereof" means materials employed upon formulation of the preparation of this invention. No particular limitation is imposed on their forms in liquid or lyophilized preparations.

In this invention, other additives employed commonly in pharmaceutical products, such as pH modifiers and extenders, can also be added as needed in addition to the essential ingredients described above.

Preferably, the pH of the preparation is adjusted to 4.0–6.0.

The final form of the preparation according to this invention is most preferably a lyophilized injection. The lyophilized injection can be formulated by a method known per se in the art. For example, the cephalosporin derivative represented by the formula (I) or a pharmaceutically acceptable salt thereof is dissolved along with lactose, citric acid and sodium chloride in injection-grade distilled water. After the pH of the solution is adjusted with an aqueous alkaline solution, the solution is filtered under sterile conditions and is then filled in predetermined amounts in vials or ampoules. The solution is then processed into a lyophilized preparation by a method known per se in the art. As an alternative, after the filtration under the sterile conditions, the solution is lyophilized into powder and the powder is then filled in predetermined amounts in vials or ampoules.

To confirm the advantageous effects of the present invention, the cephalosporin derivative represented by the formula (I) was formulated into lyophilized injectable preparations, and the external appearance and stability of the injectable preparations and the degrees of coloration of their solutions were measured.

Experiments 1–13

In each experiment, 5 ml portions of a solution with the respective ingredients dissolved therein in amounts shown in Table 1 were separately lyophilized to provide samples. The sample for the measurement of the content of the cephalosporin derivative was stored for 1 month at 45° C., while the sample for the measurement of the degree of coloration was stored for 3 months at 45° C. Upon measurement of the content and the degree of coloration, each sample was dissolved in 5 ml of injection-grade distilled water. The content was measured by HPLC, while the degree of coloration was determined by a colorimetric analysis at 450 nm wavelength. The external appearance was visually observed immediately after the lyophilization. The content was indicated in terms of percentage based on the content of the same cephalosporin derivative in the sample stored at −20° C. The results are shown in Table 2.

TABLE 1

| | Amounts of Individual Ingredients Added per Vial (g) | | | | |
|---|---|---|---|---|---|
| Experiment No. | Cephalosporin (I) | Lactose | Sodium chloride | Citric acid | Arginine HCl |
| 1 | 0.5 | 0 | 0 | 0 | 0 |
| 2 | 0.5 | 0.25 | 0 | 0 | 0 |

TABLE 1-continued

| | Amounts of Individual Ingredients Added per Vial (g) | | | | |
|---|---|---|---|---|---|
| Experiment No. | Cephalosporin (I) | Lactose | Sodium chloride | Citric acid | Arginine HCl |
| 3 | 0.5 | 0 | 0.15 | 0 | 0 |
| 4 | 0.5 | 0.25 | 0.5 | 0 | 0 |
| 5 | 0.5 | 0 | 0 | 0.015 | 0 |
| 6 | 0.5 | 0 | 0.15 | 0.015 | 0 |
| 7 | 0.5 | 0.5 | 0 | 0.015 | 0 |
| 8 | 0.5 | 0.25 | 0.15 | 0.001 | 0 |
| 9 | 0.5 | 0.25 | 0.15 | 0.015 | 0 |
| 10 | 0.5 | 0.25 | 0.05 | 0.015 | 0 |
| 11 | 0.5 | 0.25 | 0.25 | 0.015 | 0 |
| 12 | 0.5 | 0.5 | 0.15 | 0.015 | 0 |
| 13 | 0.5 | 0.25 | 0 | 0.01 | 0.25 |

TABLE 2

| | External Appearance, Content, Degree of Coloration | | |
|---|---|---|---|
| Experiment No. | Content (%) | Degree of coloration (OD) | External appearance |
| 1 | 74.2 | ≧0.5 | + |
| 2 | 86.3 | ≧0.5 | + |
| 3 | 91.4 | ≧0.5 | ± |
| 4 | 94.0 | 0.300 | ± |
| 5 | 76.6 | ≧0.5 | + |
| 6 | 91.6 | 0.485 | − |
| 7 | 86.2 | 0.435 | ± |
| 8 | 94.0 | 0.267 | ± |
| 9 | 94.0 | 0.196 | − |
| 10 | 92.4 | 0.332 | − |
| 11 | 94.0 | 0.352 | − |
| 12 | 93.4 | 0.180 | − |
| 13 | 92.1 | 0.261 | − |

In the column under "External appearance", +, ± and − are defined as follows:
+ ... Yellow,
± ... Slightly yellow, and
− ... White.

From the foregoing results, it is clear that the preparations according to the present invention (Experiment Nos. 8–13) underwent only a small reduction in the content of the cephalosporin derivative and showed excellent resistance to coloration and variations in external appearance.

The present invention will hereinafter be described in more detail by the following specific examples. It should however be borne in mind that the present invention is not limited to or by the following examples.

EXAMPLE 1

Injection-grade distilled water (40 ml) was added to the cephalosporin derivative of the formula (I) (5 g), sodium chloride (1 g), lactose (2.5 g) and citric acid (500 mg) to form a solution. After the pH of the solution was adjusted to 4.5 with 0.1 N aqueous solution of sodium hydroxide, injection-grade distilled water was added in an amount sufficient to produce 50 ml. Subsequent to filtration of the solution under sterile conditions, the filtrate was filled in 5-ml aliquots in 10-ml vials and lyophilized. The vials were thereafter hermetically capped.

EXAMPLE 2

Injection-grade distilled water (40 ml) was added to the cephalosporin derivative of the formula (I) (5 g), L-arginine hydrochloride (2.5 g), lactose (2.5 g) and citric acid (500 mg) to form a solution. After the pH of the solution was adjusted to 5.0 with 0.1 N aqueous solution of sodium hydroxide, injectiongrade distilled water was added in an amount sufficient to produce 50 ml. Subsequent to filtration of the solution under sterile conditions, the filtrate was filled in 5-ml aliquots in 10-ml vials and lyophilized. The vials were thereafter hermetically capped.

EXAMPLE 3

Injection-grade distilled water (1600 ml) was added to the cephalosporin derivative of the formula (I) (200 g), sodium chloride (60 g), lactose (100 g) and citric acid (6 g) to form a solution. After the pH of the solution was adjusted to 5.0 with 0.1 N aqueous solution of sodium hydroxide, injection-grade distilled water was added in an amount sufficient to produce 200 ml. Subsequent to filtration of the solution under sterile conditions, the filtrate was filled in 5-ml aliquots in 10-ml vials and lyophilized. The vials were thereafter hermetically capped.

We claim:

1. A preparation containing 7β-{2-(5-amino-1,2,4-thiadiazol-3-yl)-(Z)-2-fluoromethoxyiminoacetamido}-3-{(E)-3-(carbamoylmethylethylmethylammonio)-1-propen-1-yl}-3-cephem-4-carboxylate represented by the following formula:

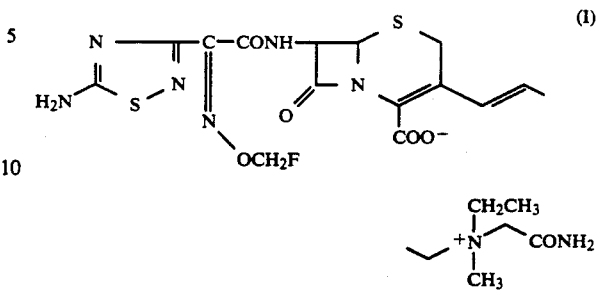

or a pharmaceutically acceptable salt thereof, and 0.1 to 1.3 parts by weight of lactose, 0.01 to 0.065 parts by weight of citric acid or a sodium salt thereof and 0.1 to 0.65 parts by weight of argninie or a hydrochloride thereof or sodium chloride, said values being per part by weight of the cephem derivative or its pharmaceutically acceptable salt.

* * * * *